United States Patent [19]

Holm

[11] Patent Number: 4,460,402
[45] Date of Patent: Jul. 17, 1984

[54] SYNERGISTIC HERBICIDE COMPOSITIONS OF PHENOXYBENZOIC ACIDS AND CYCLOHEXANEDIONES

[75] Inventor: Robert E. Holm, Belle Mead, N.J.

[73] Assignee: Rhone-Poulenc Agrochimie, Lyons, France

[21] Appl. No.: 282,201

[22] Filed: Jul. 10, 1981

[51] Int. Cl.³ .......................................... A01N 31/04
[52] U.S. Cl. ........................................ 71/98; 71/108
[58] Field of Search .................................. 71/108, 98

[56] References Cited

FOREIGN PATENT DOCUMENTS 30676 6/1981 European Pat. Off. .
62637 6/1974 Japan .
2058055 4/1981 United Kingdom .

Primary Examiner—Catherine L. Mills

[57] ABSTRACT

This invention provides synergistic herbicidal compositions of glycolate and lactate esters of phenoxybenzoic acids with cyclohexonediones. These compositions are relatively safe to soybeans and have unexpected herbicidal effectiveness against broadleaf weeds such as velvetleaf.

3 Claims, No Drawings

SYNERGISTIC HERBICIDE COMPOSITIONS OF PHENOXYBENZOIC ACIDS AND CYCLOHEXANEDIONES

BACKGROUND OF THE INVENTION

This invention is concerned with synergistic herbicidal compositions of glycolate and lactate esters of phenoxybenzoic acids with cyclohexanediones.

Glycolate and lactate esters of phenoxybenzoic acids of formula I are herbicides which are useful for both pre-emergence and post-emergence control of monocotyledon and dicotyledon weeds in crops such as soybeans, peanuts, rice, wheat and other small grains where the substituents X, $R_1$ and $R_2$ are defined as follows:

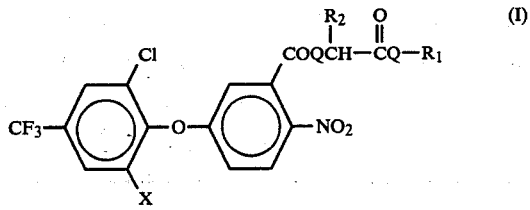

where
Q is O or S;
X is halogen (preferably Cl) or hydrogen;
$R_1$ is alkyl group of 1 to 4 carbon atoms; and
$R_2$ is hydrogen or alkyl group of 1 to 4 carbon atoms.

Cyclohexane derivatives of formula II are herbicides which are useful for post-emergence control of monocotyledon weeds in dicotyledon crops such as soybeans and peanuts where substituents $R_3$, $R_4$ $R_5$, n and Y are defined as follows:

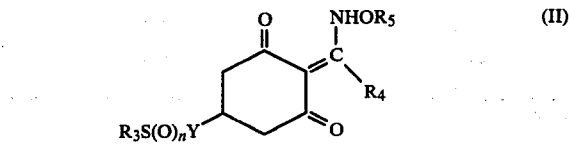

where
$R_3$ is selected from the group consisting of lower alkyl, benzyl, phenyl and substituted phenyl, e.g., with Cl, $CH_3$ or $OCH_3$;
$R_4$ is lower alkyl;
n is 0, 1 or 2;
$R_5$ is selected from the group consisting of lower alkyl (e.g., $C_1$-$C_4$ alkyl) and lower alkenyl (e.g., $C_1$-$C_4$ alkenyl); and
Y is straight or branched alkylene having 2 or 3 carbon atoms. Agronomically acceptable metal salts (Na, Ca, Cu, Fe, etc.) of the above compounds are also known herbicides.

When compounds of formula I are used post-emergence, good to excellent control of broadleaf weeds is obtained although some species are controlled more effectively than others. Grass weeds are controlled less effectively than broadleaf weeds when compounds of formula I are applied post-emergence. However, compounds of formula I show the unique property of giving pre-emergence control of both broadleaf and grass weeds following post-emergence application.

When compounds of formula II are used post-emergence, good to excellent control of grass weeds is obtained with essentially no broadleaf weed control. Compounds of formula II exhibit little or no pre-emergence activity.

SUMMARY OF THE INVENTION

This invention provides a herbicidal composition comprising at least one compound of formula I and at least one compound of formula II. Preferably, this composition consists essentially of the compounds of formulas I and II as the active herbicidal ingredients of the composition, whereby the composition is capable of being applied in a post-emergence application to a field of soybeans also containing grass weeds and broadleaf weeds, this application being sufficient to control these weeds while remaining essentially safe to the soybeans.

When compounds of formula I and formula II are mixed before application to crops and weeds, the result is an unexpected synergism in weed control activity on certain broadleaf weed species. This synergism occurs on agronomically important weed species such as sicklepod, morningglory, velvetleaf and cocklebur in situations where compounds of formula II give no control of these species and lower rates of compounds of formula I give partial control. Field results indicate that combinations of compounds of formulas I and II may allow a one time herbicide application for both broadleaf and grass weeds in crops like soybeans and peanuts. This is made possible by the broad spectrum post-emergence control of both broadleaf and grass weeds by the compounds of formulas I and II and by the residual pre-emergence activity on both broadleaf and grass weeds exhibited by compounds of formula I.

Ethoxycarbonylmethyl 5-[2-chloro-4-(trifluoromethyl)phenoxy]-2-nitrobenzoate (Compound 1), a representative example of formula 1 compounds, and BAS 9052.(POAST, a tradename of BASF) (Compound 2), a representative example of formula II compounds in a tautomeric cyclohexaneone form,

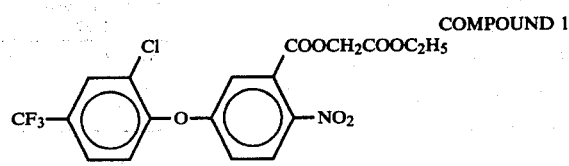

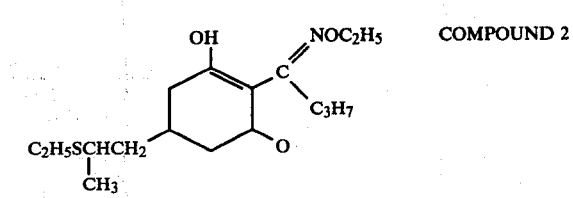

were mixed in a ratio of 1 part Compound 1 to 2 parts Compound 2. Field tests were conducted as follows:
Crops: Soybeans, corn, wheat
Weeds:
  Broadleaves: annual morningglory, velvetleaf, wild mustard, cocklebur, pigweed and sicklepod.
  Grasses: green foxtail, barnyardgrass.
Planting and Treatments: Planting was done 28 days before treatment.
Plot Design: 16' W×57' L; crops and weeds seeded in parallel rows along the length axis; direction of treatment parallel to rows; variable 100% log application rate; observations made at 100%, 50%, 25%, 12½% initial rate.

Observations: Crop injury was rated 4, 15 and 28 days after treatment and weed control 15 and 28 days after treatment.

Precipitation:
  From seeding to treatment: 2.31"
  First rain after treatment: 0.13" at 13 days
  Total through final observations: 1.31"

Air Temperatures: First 14 days after treatment:
  75°–95° F. daytime highs and 55°–70° nightime lows Standards: The standards in this test included TACKLE (a formulation of sodium acifluorfen and a tradename of the Mobile Oil Corporation) and BASAGRAN (a formulation of bentazon and a tradename of BASF).

The results of this test are set forth in Tables I–VII.

TABLE I

1° Post, Series II Log*

Mean Percent Crop Injury - 5 days

| Treatments | Soybeans | | | | Corn | | | | Wheat | | | |
|---|---|---|---|---|---|---|---|---|---|---|---|---|
| | 100% | 50% | 25% | 12.5% | 100% | 50% | 25% | 12.5% | 100% | 50% | 25% | 12.5% |
| 1. Untreated Control | 0 | 0 | 0 | 0 | 0 | 0 | 0 | 0 | 0 | 0 | 0 | 0 |
| 2. TACKLE at 1⅛ | 29.2 | 23.5 | 17.2 | 13.5 | 50.0 | 30.0 | 23.8 | 17.2 | 45.0 | 25.5 | 16.7 | 5.7 |
| 3. BASAGRAN at 2¼ | 4.5 | 1.2 | 0.2 | 0 | 4.5 | 0.5 | 0 | 0 | 7.5 | 0.8 | 0 | 0 |
| 4. Compound 1 at 1⅛ | 29.2 | 23.0 | 18.0 | 14.2 | 33.8 | 24.2 | 17.2 | 14.8 | 38.2 | 19.2 | 9.2 | 3.3 |
| 5. Compound 2 at 2¼ | 2.2 | 0 | 0 | 0 | 10.0 | 5.5 | 3.8 | 1.8 | 3.8 | 1.5 | 0 | 0 |
| 6. Compound 1/Compound 2 at 1⅛/2¼ | 33.2 | 26.2 | 21.2 | 14.8 | 56.2 | 33.8 | 23.0 | 17.2 | 68.8 | 51.2 | 36.2 | 18.8 |

*Rates are given as % of initial rate(s)

TABLE II

1° Post, Series II Log*

Mean Percent Crop Injury @ 15 days

| Treatments | Soybeans | | | | Corn | | | |
|---|---|---|---|---|---|---|---|---|
| | 100% | 50% | 25% | 12.5% | 100% | 50% | 25% | 12.5% |
| 1. Untreated Control | | | | | | | | |
| 2. TACKLE at 1⅛ | 8.8 | 0 | 0 | 0 | 2.5 | 0 | 0 | 0 |
| | 23.8 | 26.2 | 22.0 | 6.5 | 51.5 | 35.0 | 23.2 | 25.2 |
| 3. BASAGRAN at 2¼ | 4.2 | 2.5 | 2.5 | 3.8 | 5.0 | 1.2 | 7.5 | 0.8 |
| 4. Compound 1 at 1⅛ | 28.8 | 20.0 | 8.5 | 5.2 | 30.0 | 22.5 | 15.0 | 11.8 |
| 5. Compound 2 at 2¼ | 8.8 | 5.8 | 0 | 0 | 100.0 | 99.0 | 88.8 | 82.5 |
| 6. Compound 1/Compound 2 at 1⅛/2¼ | 47.5 | 36.5 | 25.8 | 18.5 | 100.0 | 93.8 | 87.0 | 75.0 |

*Rates are given as % of initial rate(s)

TABLE III

1° Post, Series II Log*

Mean Percent Crop Injury @ 28 days

| Treatments | Soybeans | | | | Corn | | | |
|---|---|---|---|---|---|---|---|---|
| | 100% | 50% | 25% | 12.5% | 100% | 50% | 25% | 12.5% |
| 1. Untreated control | 0 | 0 | 0 | 0 | 0 | 0 | 0 | 0 |
| 2. TACKLE at 1⅛ | 14.5 | 12.8 | 8.5 | 4.0 | 4.3 | 2.3 | 1.0 | 0 |
| 3. BASAGRAN at 2¼ | 1.0 | 0 | 0 | 0 | 1.2 | 0 | 0 | 0 |
| 4. Compound 1 at 1⅛ | 16.0 | 12.8 | 7.8 | 3.2 | 4.5 | 3.0 | 1.2 | 0 |
| 5. Compound 2 at 2¼ | 0.8 | 0 | 0 | 0 | 100.0 | 100.0 | 98.8 | 95.2 |
| 6. Compound 1/Compound 2 at 1⅛/2¼ | 23.0 | 16.2 | 13.0 | 9.8 | 100.0 | 99.8 | 96.5 | 82.5 |

*Rates are given as % initial rate(s)

TABLE IV

1° Post, Series II Log*

Mean Percent Weed Control @ 15 Days

| Treatments | Wild Mustard | | | | Barnyardgrass | | | | Pigweed | | | |
|---|---|---|---|---|---|---|---|---|---|---|---|---|
| | 100% | 50% | 25% | 12.5% | 100% | 50% | 25% | 12.5% | 100% | 50% | 25% | 12.5% |
| 1. | 0 | 0 | 0 | 0 | 0 | 0 | 0 | 0 | 0 | 0 | 0 | 0 |
| 2. | 100.0 | 100.0 | 100.0 | 97.5 | 47.5 | 17.5 | 6.2 | 1.2 | 100.0 | 100.0 | 100.0 | 99.0 |
| 3. | 100.0 | 100.0 | 100.0 | 100.0 | 50.0 | 35.0 | 18.8 | 7.5 | 100.0 | 100.0 | 95.8 | 63.8 |
| 4. | 100.0 | 100.0 | 100.0 | 100.0 | 36.2 | 12.5 | 2.5 | 0 | 100.0 | 100.0 | 100.0 | 100.0 |

TABLE IV-continued

1° Post, Series II Log*
Mean Percent Weed Control @ 15 Days

| Treatments | Wild Mustard 100% | 50% | 25% | 12.5% | Barnyardgrass 100% | 50% | 25% | 12.5% | Pigweed 100% | 50% | 25% | 12.5% |
|---|---|---|---|---|---|---|---|---|---|---|---|---|
| 5. | 6.7 | 0 | 0 | 0 | 100.0 | 100.0 | 99.8 | 96.5 | 0 | 0 | 0 | 0 |
| 6. | 100.0 | 100.0 | 100.0 | 100.0 | 100.0 | 99.5 | 97.2 | 93.0 | 100.0 | 100.0 | 100.0 | 100.0 |

*Rates are given as % initial rate(s)

TABLE V

1° Post, Series II Log*
Mean Percent Weed Control @ 15 Days

| Treatments | Morningglory 100% | 50% | 25% | 12.5% | Velvetleaf 100% | 50% | 25% | 12.5% | Cocklebur 100% | 50% | 25% | 12.5% | Sicklepod 100% | 50% | 25% | 12.5% |
|---|---|---|---|---|---|---|---|---|---|---|---|---|---|---|---|---|
| 1. | 0 | 0 | 0 | 0 | 0 | 0 | 0 | 0 | 0 | 0 | 0 | 0 | 0 | 0 | 0 | 0 |
| 2. | 100.0 | 95.8 | 91.2 | 85.8 | 98.7 | 88.3 | 81.7 | 66.7 | 100.0 | 94.0 | 84.5 | 70.0 | 60.0 | 22.5 | 7.5 | 0 |
| 3. | 50.5 | 25.0 | 0 | 0 | 100.0 | 97.8 | 95.2 | 85.0 | 100.0 | 100.0 | 92.5 | 78.8 | 8.8 | 0 | 0 | 0 |
| 4. | 99.8 | 95.0 | 89.5 | 80.0 | 99.2 | 92.0 | 83.0 | 62.5 | 100.0 | 99.0 | 95.8 | 87.0 | 90.0 | 72.5 | 50.0 | 26.2 |
| 5. | 0 | 0 | 0 | 0 | 2.5 | 0 | 0 | 0 | 0 | 0 | 0 | 0 | 0 | 0 | 0 | 0 |
| 6. | 100.0 | 99.8 | 92.0 | 85.8 | 100.0 | 99.7 | 92.7 | 91.0 | 100.0 | 99.5 | 98.2 | 93.2 | 88.8 | 78.8 | 71.2 | 45.5 |

*Rates are given as % initial rate(s)

TABLE VI

1° Post, Series II Log*
Mean Percent Weed Control @ 28 Days

| Treatments | Wild Mustard 100% | 50% | 25% | 12.5% | Barnyardgrass 100% | 0% | 25% | 12.5% | Pigweed 100% | 50% | 25% | 12.5% |
|---|---|---|---|---|---|---|---|---|---|---|---|---|
| 1. | 0 | 0 | 0 | 0 | 0 | 0 | 0 | 0 | 0 | 0 | 0 | 0 |
| 2. | 100.0 | 100.0 | 97.5 | 91.2 | 11.2 | 3.8 | 0 | 0 | 97.5 | 97.5 | 93.8 | 94.5 |
| 3. | 100.0 | 100.0 | 100.0 | 80.0 | 9.2 | 0 | 0 | 0 | 97.5 | 96.2 | 83.0 | 40.0 |
| 4. | 100.0 | 100.0 | 100.0 | 100.0 | 7.5 | 0 | 0 | 0 | 100.0 | 100.0 | 100.0 | 100.0 |
| 5. | 0 | 0 | 0 | 0 | 100.0 | 100.0 | 100.0 | 99.8 | 0 | 0 | 0 | 0 |
| 6. | 100.0 | 100.0 | 100.0 | 100.0 | 100.0 | 100.0 | 99.2 | 98.5 | 100.0 | 100.0 | 100.0 | 100.0 |

*Rates are given as % initial rate(s)

TABLE VII

1° Post, Series II Log*
Mean Percent Weed Control @ 28 Days

| Treatments | Morningglory 100% | 50% | 25% | 12.5% | Velvetleaf 100% | 50% | 25% | 12.5% | Cocklebur 100% | 50% | 25% | 12.5% | Sicklepod 100% | 50% | 25% | 12.5% |
|---|---|---|---|---|---|---|---|---|---|---|---|---|---|---|---|---|
| 1. | 0 | 0 | 0 | 0 | 0 | 0 | 0 | 0 | 0 | 0 | 0 | 0 | 0 | 0 | 0 | 0 |
| 2. | 99.5 | 90.2 | 76.8 | 60.8 | 94.3 | 82.3 | 59.3 | 38.3 | 98.8 | 87.5 | 77.5 | 53.0 | 47.5 | 22.5 | 5.0 | 5.0 |
| 3. | 37.5 | 8.8 | 0 | 0 | 100.0 | 97.5 | 93.8 | 75.0 | 100.0 | 100.0 | 91.5 | 77.5 | 5.0 | 0 | 0 | 0 |
| 4. | 100.0 | 95.5 | 80.0 | 69.5 | 98.8 | 87.2 | 61.2 | 38.8 | 100.0 | 99.2 | 95.5 | 85.8 | 83.2 | 63.2 | 22.5 | 7.5 |
| 5. | 0 | 0 | 0 | 0 | 0 | 0 | 0 | 0 | 0 | 0 | 0 | 0 | 0 | 0 | 0 | |
| 6. | 100.0 | 98.0 | 87.0 | 77.0 | 100.0 | 97.3 | 88.7 | 82.3 | 100.0 | 99.0 | 96.5 | 91.8 | 85.0 | 77.5 | 60.0 | 41.8 |

*Rates are given as % initial rate(s)

The combination of Compounds 1 and 2 showed evidence of synergistic interactions in broadleaf weed control (e.g., compare lower application rates in Treatments 4, 5 and 6 in Tables V and VII on, particularly, velvetleaf and also cocklebur and morninggglory at 15 and 28 days).

The compounds of formula II may be obtained from commercially available sources or made by techniques known by those of ordinary skill in the art. It will be understood that formula II is intended to represent either cyclohexanone compounds as illustrated or the cyclohexenone tautomers of these compounds.

The compounds of formula I may also be prepared by techniques known by those of ordinary skill in the art. For example, the compound, ethoxycarbonyl methyl 5-[2-chloro-4-(trifluoromethyl)phenoxy]-2-nitrobenzoate, has been prepared as follows: To a stirred solution of ethyl glycolate (83.7 g, 0.8 mole) and 5-[2-chloro-4-(trifluoromethyl)phenoxy]-2-nitrobenzoyl chloride (306 g, 0.8 mole) in toluene (800 ml) cooled in an ice bath was added triethylamine (80.8 g, 0.8 mole) dropwise. The exotherm was controlled below 35° C. during addition. The reaction temperature was raised to 62° C. and held for five hours. After cooling the precipitate was filtered. The toluene solution was then washed with 5% sodium hydroxide solution followed by saturated sodium chloride solution. The dried toluene solution was stripped on a rotary evaporator to give 225 g of a brown oil. Vapor phase chromatographic—mass spectral analysis showed that in addition to the desired product there was about 1% of ethyl 5-[2-chloro-4-(trifluoro-methyl)-phenoxy]-2-nitrobenzoate and about 9% of ethoxycarbonyl-methoxycarbonylmethyl 5-[2-chloro-4-(trifluoromethyl)phenoxy]-2-nitrobenzoate. The product can be further purified by crystallization from hexane to give an off-white solid.

m.p. 58°–59° C.

I.R. (Neat): C=O, 1745 and 1760 cm$^{-1}$

NMR (CDCl$_3$): triplet 1.30 ppm (3H, J=7.2 Hz); quartet 4.33 ppm (2H, J=7.2 Hz); singlet 4.92 (2H), complex multiplet 7.1-8.1 ppm (5H) and doublet 8.21 ppm (1H, J=9.0 Hz).

A number of compounds of this formula I may alternatively be prepared by displacement of an active halogen (e.g. Haloalkyl X) with the salt of an acid

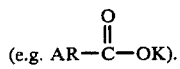

The following is an example of such a procedure.

To a stirred solution of 85% potassium hydroxide (0.66 g, 0.01 mole) in ethanol (25 ml) was added 5-[2-chloro-4-(trifluoromethyl)phenoxy]-2-nitrobenzoic acid. To this mixture was then added ethyl bromoacetate (1.67 g, 0.01 mole) at 30° C. The temperature was raised to 70° C. and maintained for 18 hours. The cooled solution was poured into water and the resulting oil solidified to an off-white solid which was filtered and dried to give 3.85 g (86% yield), m.p. 55°-6° C.

A still further alternative synthesis is shown by the following reaction scheme:

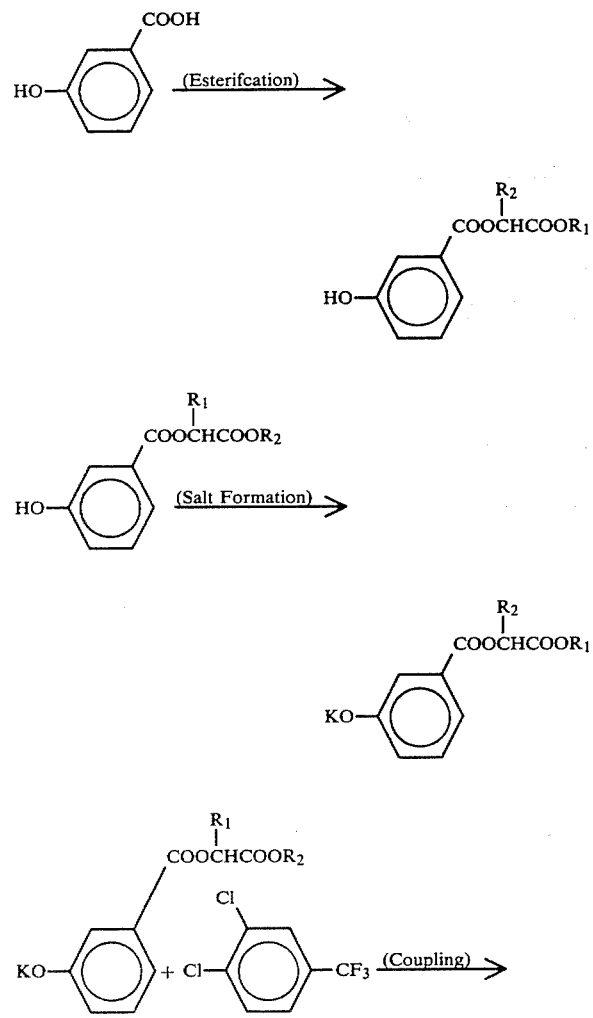

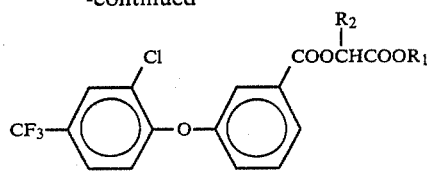

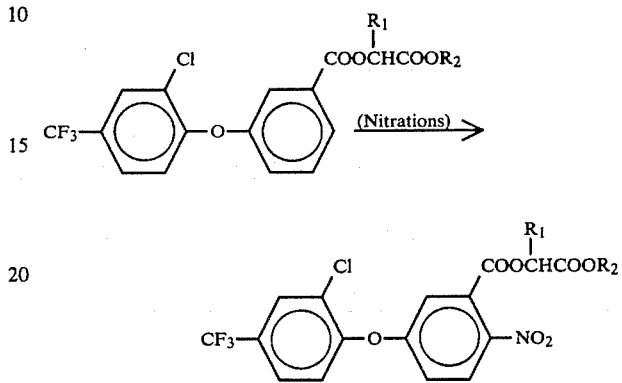

In addition to compound 1, further representative examples of compounds according to formula I include methoxycarbonylmethyl 5-[2-chloro-4-(trifluoromethyl)phenoxy]-2-nitrobenzoate, methoxycarbonyl-1-ethyl 5-[2-chloro-4-(trifluoromethyl)phenoxy]-2-nitrobenzoate and ethoxycarbonyl-1-ethyl 5-[2-chloro-4-(trifluoromethyl)phenoxy]-2-nitrobenzoate.

In addition to Compound 2, further representative examples of compounds according to formula II include the following:

2-[1-(methoxyimino)butyl]-5-[2-(ethylthio)propyl]-3-hydroxy-2-cyclohexene-1-one

2-[2-(ethoxyimino)propyl]-5-[2-(ethylthio)propyl]-3-hydroxy-2-cyclohexen-1-one

2-[1-(ethoxyimino)butyl]-5-[2-(methylthio)propyl]-3-hydroxy-2-cyclohexene-1-one

2-[1-(ethoxyimino)butyl]-5-[2-(parachlorophenylthio)-propyl]-3-hydroxy-2-cyclohexene-1-one.

The composition of the present invention may preferably contain compounds according to formula I in a ratio of from about 1:1 to about 1:3 on a weight basis with respect to compounds of formula II. Most especially, this ratio is about 1:2.

In addition to compounds of formulae I and II, the compositions of the present invention also preferably contain an agronomically acceptable carrier. These compositions may be applied directly to the soil and plants. The compositions can be applied as granulars or dusts; as liquid sprays, or as gas-propelled sprays and can contain, in addition to a carrier, additives such as emulsifying agents, binding agents, gases compressed to the liquid state, odorants, stabilizers, and the like. A wide variety of liquid and solid carriers can be used. Non-limiting examples of solid carriers include talc, bentonite, diatomaceous earth, pyrophyllite, fullers earth, gypsum, flours derived from cotton seeds and nut shells, and various natural and synthetic clays having a pH not exceeding about 9.5. Non-limiting examples of liquid carriers include water, organic solvents such as alcohols, ketones, light oils, and medium oils and vegetable oils such as cottonseed oil.

In practice, herbicidal application is measured in terms of pounds of herbicide applied per acre. The compounds of formulae I and II are effective herbicides when applied in herbicidal amounts, i.e., at rates between about 0.03 pound and about 10 pounds per acre.

The composition of the present invention may be particularly advantageous when used to control weeds in field of crops which are relatively tolerant thereto. For instance, the foregoing data demonstrates that certain crop species are more tolerant to this composition than certain grass or broadleaf weed species. The herbicidal compositions of the present invention are particularly useful when applied in post-emergence applications to control broadleaf weeds, e.g., velvetleaf, cocklebur, sicklepod, wild mustard and pigweed and grasses, e.g., green foxtail and barnyardgrass, in soybean fields. In such post-emergence applications the compounds of formula I are preferably applfied at rates from about ⅛ to about ¾ lbs/acre and the compounds of formula II are preferably applied at rates from about ¼ to about 1.5 lb/acre.

What is claimed is:

1. A herbicidal composition comprising a first compound having the formula:

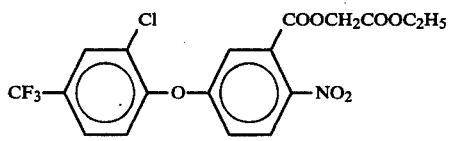

and a second compound having the formula:

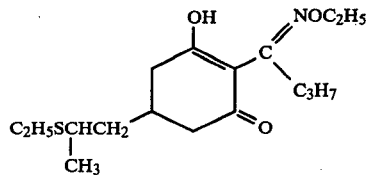

wherein the second compound also may be in the form of agronomically acceptable metal salts, and wherein the ratio by weight of said first compound to said second compound is about 1 to 2.

2. A method for controlling unwanted plants which comprises applying to said plants in a post-emergence application a herbicidally effective amount of a composition according to claim 1, wherein said application is to a field comprising soybeans and at least one broadleaf weed species selected from velvetleaf and sicklepod.

3. A method for controlling velvetleaf and sicklepod weeds growing in soybean field comprising applying to said field a post-emergence application of a herbicidal composition comprising a first compound of the formula:

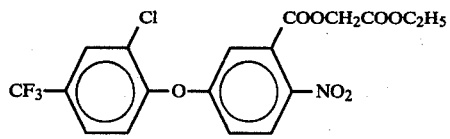

and a second compound of the formula

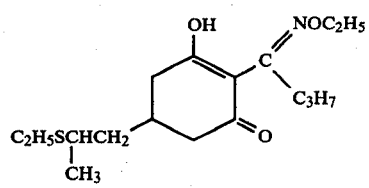

wherein said first compound is applied at a rate from about ⅛ to about ¼ lb/acre and said second compound is applied at a rate from about ¼ to about ½ lb/acre, wherein the second compound also may be in the form of agronomically acceptable metal salts, and wherein the ratio by weight of said first compound to said second compound is about 1 to 2.

* * * * *